United States Patent [19]

Bible et al.

[11] Patent Number: 5,692,530
[45] Date of Patent: Dec. 2, 1997

[54] BRAIDED DENTAL FLOSS

[75] Inventors: Kenan Oris Bible, Del Rio; Edward Sherman; Lloyd Etter, both of Morristown, all of Tenn.

[73] Assignee: Anchor Advance Products, Inc., Knoxville, Tenn.

[21] Appl. No.: 532,004

[22] Filed: Sep. 21, 1995

[51] Int. Cl.$^6$ .................................................. A61C 15/00
[52] U.S. Cl. ........................... 132/321; 132/323; 132/329
[58] Field of Search ..................................... 132/321, 323, 132/324, 325, 326, 327, 329, 328

[56] References Cited

U.S. PATENT DOCUMENTS

| | | | |
|---|---|---|---|
| 3,538,230 | 11/1970 | Pader et al. | 424/50 |
| 3,699,979 | 10/1972 | Muhler et al. | 132/89 |
| 3,771,536 | 11/1973 | Dragan | 132/89 |
| 3,800,812 | 4/1974 | Jaffe | 132/89 |
| 3,830,246 | 8/1974 | Gillings | 132/89 |
| 3,837,351 | 9/1974 | Thornton | 132/89 |
| 3,838,702 | 10/1974 | Standish et al. | 132/321 |
| 3,897,795 | 8/1975 | Engel | 132/89 |
| 3,943,949 | 3/1976 | Ashton et al. | 132/89 |
| 4,029,113 | 6/1977 | Guyton | 132/91 |
| 4,033,365 | 7/1977 | Klepak | 132/89 |
| 4,142,538 | 3/1979 | Thornton | 132/89 |
| 4,187,390 | 2/1980 | Gore | 174/102 |
| 4,215,478 | 8/1980 | Thomas | 433/25 |
| 4,256,806 | 3/1981 | Snyder | 428/378 |
| 4,265,258 | 5/1981 | Eaton, II | 132/321 |
| 4,270,556 | 6/1981 | McAllister | 132/89 |
| 4,304,245 | 12/1981 | Lichfield | 132/89 |
| 4,385,093 | 5/1983 | Hubis | 428/316.6 |
| 4,414,990 | 11/1983 | Yost | 132/91 |
| 4,478,665 | 10/1984 | Hubis | 156/229 |
| 4,645,662 | 2/1987 | Nakashima et al. | 424/52 |
| 4,832,063 | 5/1989 | Smole | 132/321 |
| 4,836,226 | 6/1989 | Wolak | 132/321 |
| 4,996,056 | 2/1991 | Blass | 424/443 |
| 4,998,978 | 3/1991 | Varum | 132/321 |
| 5,033,488 | 7/1991 | Curtis et al. | 132/321 |
| 5,038,805 | 8/1991 | Lee | 132/321 |
| 5,311,889 | 5/1994 | Ringle et al. | 132/321 |
| 5,407,623 | 4/1995 | Zachariades et al. | 264/119 |

*Primary Examiner*—Gene Mancene
*Assistant Examiner*—Pedro Philogene
*Attorney, Agent, or Firm*—Godfrey & Kahn, S.C.

[57] ABSTRACT

A braided dental floss having increased tensile strength, reduced likelihood of fraying and improved cleaning comprising multiple braided threads of nylon, polyester, polyethylene, PFA, PTFE, Dacron®, polypropylene or mixtures thereof.

1 Claim, 1 Drawing Sheet

U.S. Patent     Dec. 2, 1997     5,692,530
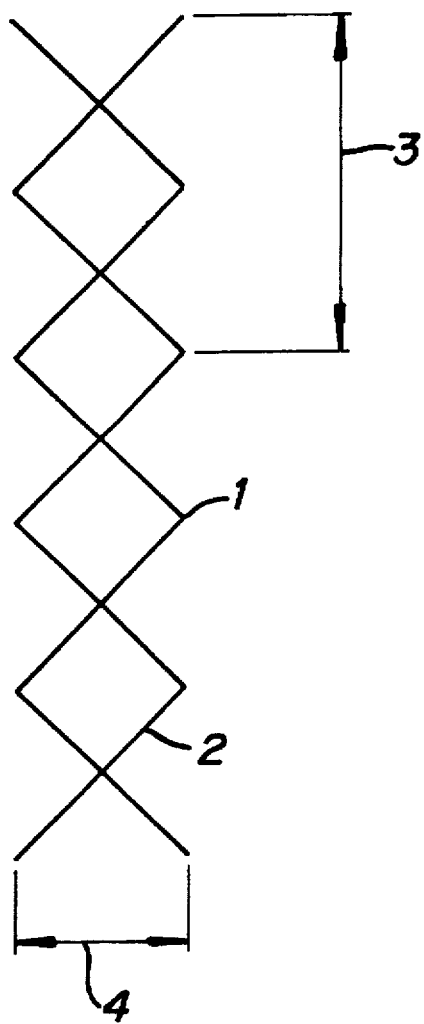
FIG_1
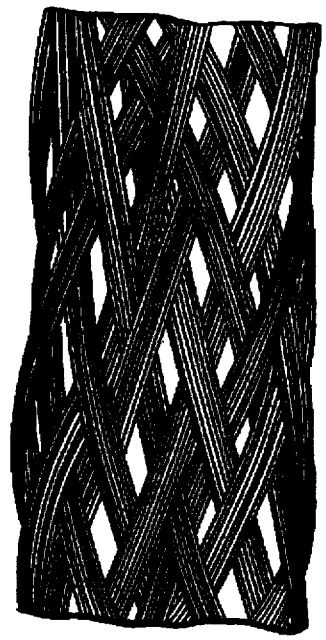
FIG_2

BRAIDED DENTAL FLOSS

FIELD OF THE INVENTION

The present invention relates generally to dental cleaning floss and more particularly to a braided dental floss providing improved characteristics.

BACKGROUND OF THE INVENTION

It should be understood that the use of the term "dental floss" hereinafter is intended to encompass dental filaments, tapes and any similar article.

The removal of plaque and entrapped food particles reduces: cavities; the tendency towards gingivitis; and mouth odor. It also generally improves oral hygiene. Conventional brushing of teeth is not particularly effective in removing entrapped food particles from crevices between the teeth and/or removing plaque which enables bacteria to adhere to teeth.

The interproximal regions are of concern to the dental profession where continual prophylaxis should be maintained to ensure the greatest resistance to deteriorating conditions. Particles of food (carbohydrates, meat fibers, etc.) are trapped in these regions and often become incapable of removal by natural reflexes. Subsequent disintegration of these food particles, if not physically removed, provide a media for detrimental microorganisms which give off acids or enzymes which cause acid formation, and therefore account for deteriorating conditions in these interproximal regions.

Dental floss is commonly used to clean and remove food, plaque and tarter build-up from around and between teeth. Various forms of dental floss have been proposed and/or employed for cleaning the interproximal areas and other areas not accessible by a toothbrush. Conventional dental floss comprises a filament of a deformable or non-deformable material that is inserted between teeth thereby allowing cleaning of the teeth as the floss is moved along the tooth surface. The most common type of floss on the market is in the form of a small diameter, smooth surfaced twisted multi-filament strand that is pulled up and down and lengthwise, between teeth, against tooth surfaces.

Other types of dental floss have been proposed including the floss shown in U.S. Pat. No. 4,142,538 to Thornton, which relates to a tooth cleaner comprising a continuous length of textured yarn formed from a plurality of deformed filaments. The yarn is coated throughout its length with a hardened covering which is stated to render it effective to clean teeth.

U.S. Pat. No. 4,270,556 to McAllister relates to a device for cleaning teeth comprising a thin flexible stainless steel strip which has been perforated in such a manner that peripheral raised ridges are formed around the perforations on the lateral surfaces of the strip.

U.S. Pat. No. 4,998,978 to Varum relates to a strip for cleaning teeth comprising cross strands in a structural arrangement that is stated to apply an improved scrubbing action to the surface of the teeth. The strands are arranged in the strip in patterns that present them angularly or across the longitudinal length of the strip so that the cross ridges formed by the strands provide a scrubbing action on the surfaces of the teeth.

U.S. Pat. No. 4,836,226 to Wolak relates to an endless article for dislodging residual food particles, cleaning away plaque and removing tarter from between teeth comprising an endless segment of an elastic material having a uniform cross section. The endless segment has a directionally effective abrasive surface and is graspable by a pair of hands.

U.S. Pat. No. 3,699,979 to Muhler et al. relates to articles for cleaning and polishing the interproximal surfaces of teeth comprising a coated dental floss and tape having fibrous material twisted together to form either a single thread or tape capable of being inserted between teeth, a water soluble coating material adhered to the fibrous material and a dental polishing and cleaning agent added to the coating material and adhering to the fibrous material. Although the term "woven" is used in the patent, it is clear from the description and figures that the floss contains strands that are conventionally twisted and not in any way braided.

U.S. Pat. No. 3,837,351 to Thornton relates to an interdental tooth cleaner comprising a continuous length of textured yarn that has been coated with a hardened resin to increase its stiffness and memory. The yarn may be formed from nylon filaments in which the filaments have been processed to permanently crinkle or otherwise deform them from their normal straight condition.

U.S. Pat. No. 3,897,795 to Engel relates to a dental floss comprising a plurality of fibers which are coated or bonded with a soap and/or detergent. The floss can be made by first forming a paste of soap, detergent or a mixture thereof into which various therapeutic ingredients are dispersed.

U.S. Pat. No. 3,943,949 to Ashton et al. relates to a dental floss comprising a plurality of twisted filaments of a substrate material formed into a larger thread of a sufficiently small diameter, the filaments being coated with water-insoluble wax with spray-dried flavor particles adhered to the water-insoluble wax.

As the above described references show, there is a need for a flexible dental cleaning floss having increased cleaning and polishing properties, improved tensile strength, greater resistance to fraying and superior comfort vis-a-vis a user's gums.

SUMMARY OF THE INVENTION

It is therefore an object of the invention to provide an improved flexible dental floss which provides substantially increased cleaning and polishing properties over the prior art.

It is a further and related object of the invention to provide a flexible dental floss having increased tensile strength and reduced fraying when compared to the prior art.

It is yet another object of the present invention to provide a dental floss which is gentler on users' gums than the prior art.

These and other objects and advantages of the present invention will become apparent from the detailed description and accompanying drawings.

The dental cleaning floss of the present invention comprises multiple braided threads of one or more materials. The invention differs from the prior art in that multiple strands are first twisted together to form threads which are then braided together to form a structured cohesive floss rather than a loosely formed thread of twisted strands relying on wax or good fortune to hold it together.

The dental floss of the present invention comprises a plurality of threads each formed from at least one strand of material. Preferred materials for forming strands are nylon, polyester, polyethylene, PFA, PTFE, Dacron® and polypropylene having a diameter of about 0.0002 to 0.003 inches. Preferably, the dental floss of the present invention comprises an odd number of threads having "pics" per inch in the range from about 15 to about 50 (a pic is the number of crossing braids per inch). The tensile strength of the braided threads formed into floss is generally between about 5 and 25 pounds. This results in a dental floss with improved cleaning capabilities, increased tensile strength and reduced fraying.

In one embodiment of the invention, the dental floss is coated with wax. In other embodiments the floss is coated with a polymer containing flavor particles and/or colorants.

The braiding of threads to form a floss in accordance with the present invention provides numerous advantages over unbraided, prior art floss including:

The sharpness of the present floss is reduced significantly, resulting in less discomfort to a user's gums.

Tensile strength can be controlled by varying the dimensions of the threads, the number of voids and/or by using different materials to meet a user's specific needs. A lower tensile strength variant can be created for people with problematic dental work.

Individual strands or threads can be coated to assure better control of flavoring and medicinal additives rather than coating the entire floss.

Braiding causes natural voids between threads which can be adjusted depending on the number of pics per inch or size of threads, for example. A larger number of pics decreases the amount of void area with the floss becoming very similar to a tape material. The fewer pics per inch, the larger the void area becomes between strands. The "elasticity" of the material can also be controlled by the number of pics. The fewer pics per inch, the greater the elasticity. Increased elasticity can improve the ability to insert the floss between tightly spaced teeth.

The natural void areas caused by braiding allow for greater adhesion and dispersion of coating and flavoring additives than the prior art.

Braiding permits the use of dissimilar materials to enhance the overall characteristics of the final floss material as needed. For example, certain materials carry additives better while others impart greater lubricity.

In sum, the present invention represents a significant improvement over the prior art. The use of braiding yields an improvement over non-braided materials because floss made in accordance with the present invention is subject to less fraying, is easy to insert between teeth, is easy on the gums after insertion, and improves cleaning between teeth. The use of braiding also ensures that there are voids between threads which can be used for carrying flavorings and/or medicinal agents and more effectively removing particulate matter from between teeth than materials without such voids.

BRIEF DESCRIPTION OF THE DRAWINGS

In the drawings:

FIG. 1 is a schematic view of two threads of a floss braided according to an embodiment of the invention; and FIG. 2 is a microphotograph of a braided dental floss according to an embodiment of the present invention.

DETAILED DESCRIPTION OF THE INVENTION

The present invention comprises multiple strands of nylon, polyester, polyethylene, PFA, PTFE, Dacron®, polypropylene, and mixtures thereof (any of which may be uniaxially or biaxially stretched) braided together to form a dental floss. FIG. 1 is a schematic representation of one embodiment of the present invention showing two threads 2 braided together to form the floss 1. (See also FIG. 2 which depicts 10 strands formed into threads, 13 of which are braided to form a floss having 30 pics per inch and a denier of about 390.) The braiding of the threads, among other things, increases the tensile strength of the floss and its cleaning properties.

Preferably, the dental floss of the present invention comprises a plurality of threads which threads have from 1 to 50 strands, each strand having a diameter of between about 0.0002 and about 0.003 inches and a fineness of between about 1 and about 50 denier. Optimally, 10 strands make up each thread with each strand having a diameter of 0.0005 inches and a fineness of about 3 denier. Where more than one strand makes up a thread, the strands are twisted together, preferably at a rate of about 3 turns per inch. The floss of the present invention preferably comprises an odd number of threads ranging from 3 to 21, with each thread having a diameter of about 0.0002 to 0.01 inches and a fineness of about 10 to about 50 denier. Optimally, each thread is about 0.005 inches in diameter and about 30 denier. The finished floss of the present invention preferably has a thickness from about 0.0006 to about 0.003 inches and a width from about 0.03 to about 0.150 inches, fineness of about 200 to about 1250 denier and a tensile strength between about 5 to about 25 lbs. Optimally, the thickness of the floss is about 0.0015 to about 0.002 inches and the width of about 0.04 to about 0.06 inches with a fineness of about 390 denier. In addition, the number of pics per inch preferably range from about 15 to about 50. (The pic distance 3 and floss width 4 are depicted in FIG. 1.)

In one embodiment of the present invention, the dental floss is coated with wax. The coating process can be done either before or after the braiding process. The application of a coating after the braiding process would necessarily coat all of the strands and/or threads with the same material. Coating before braiding allows the application of specific materials (e.g., fluoride, etc.) to specific strands and/or threads.

The coating process also allows individual strands and/or threads to be colored. For example, a food additive colorant could be used to provide a visual stimulus to the consumer indicating the type of material and flavoring being used (i.e., green for mint, red for cinnamon).

When certain materials are used (e.g., nylon), it may be necessary to increase lubricity. In such situations, wax can be employed to improve the lubricity. With certain other materials, e.g., PTFE, the wax can act to increase the frictional qualities, i.e., as an anti-lubricant. Wax can also be used as a carrier for flavorings and medicinal additives.

A wide variety of waxes may be employed. The wax chosen should be suitable and safe for all use, and should be easily applied. Suitable waxes include natural waxes (i.e. from insects, animals or plants), petroleum waxes and synthetic waxes. In one preferred embodiment of the present invention the wax is a beeswax. Beeswax has certain advantages when used to coat dental floss. It is a natural product with no known adverse indications for human use and therefore is more acceptable, particularly for an article which is to be used in the mouth. In addition, beeswax provides satisfactory coating characteristics and also beneficial friction characteristics. Furthermore, beeswax is readily available. The amount of wax employed is preferably in the range of about 5 to about 30% by weight of the total weight of the dental floss. The wax may also be a microcrystalline wax.

Flavor agents may also be used. The use of a flavored dental floss as opposed to an unflavored floss provides aesthetic advantages. This can make the floss more pleasant to use, to thereby encourage better oral hygiene practices. Preferably, flavor particles are spray dried onto the floss. The particles consist essentially of a flavor oil dispersed in a matrix of a water soluble medium. The coating preferably comprises about 1 to 10% by weight of the dental floss. The spray-dried flavor particles may comprise about 0.5 to 12% by weight of the dental floss.

In another embodiment, the strands or threads are impregnated with a polymeric coating containing spray-dried flavor particles consisting essentially of a flavor oil dispersed in a matrix of a water-soluble medium with the water-soluble medium being capable of being dissolved by the saliva in the oral cavity when the floss is applied to the teeth thereby releasing the flavor to the teeth and oral cavity.

In yet another embodiment, the strands or threads are impregnated with a polymeric coating containing spray-dried flavor particles, wherein the polymeric coating is:

a. alkyl monoesters of poly(methyl vinyl ether/maleic acid) of the formula:

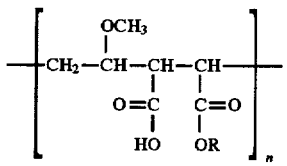

wherein R is an alkyl group containing from 1 to 4 carbon atoms or hydrogen and wherein n is from about 3,000 to 3,400;

b. polyvinyl pyrrolidones of the formula:

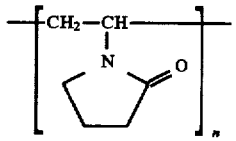

wherein n is from about 100 to 360;

c. acrylamide/acrylate/butylaminoethyl methacrylate polymers;

d. vinyl acetate/crotonic acid/vinyl neodecanoate terpolymers;

e. vinyl acetate/crotonic acid copolymers; and f. terpolyamides comprised of the copolymerization products of dicarboxylic acid-diamine reaction product, a second but dissimilar dicarboxylic acid-diamine reaction product and a lactim wherein said terpolyamides have a molecular weight of from about 12,000 to about 24,000.

In another embodiment, the polymeric coating is an alkyl monoester of poly(-methyl vinyl ether/maleic acid) of the formula:

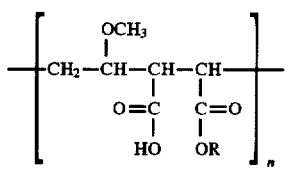

wherein R is selected from alkyl groups containing 1 to 4 carbon atoms and hydrogen and n is from 3000 to 3400.

In yet another embodiment, the polymeric coating is a polyvinyl pyrrolidone of the formula:

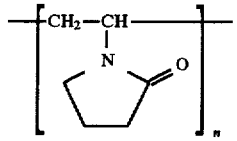

wherein n is from about 100 to 360.

The polymeric coating may also comprise an acrylamide/acrylate/-butylaminoethyl methacrylate polymer, a vinyl acetate/crotonic acid/-vinyl neodecanoate terpolymer, or a vinyl acetate/crotonic acid copolymer.

Alternatively, the polymeric coating may comprise a terpolyamide comprising the copolymerization product of a dicarboxylic acid-diamine reaction product, a second but dissimilar dicarboxylic acid-diamine reaction product and a lactim wherein said terpolyamides have a molecular weight of from about 12,000 to about 24,000.

In still another embodiment, the polymeric coating is:

a. alkyl monoesters of poly(methyl vinyl ether/maleic acid) of the formula:

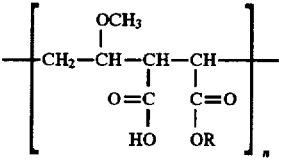

wherein R is an alkyl group containing from 1 to 4 carbon atoms or hydrogen and wherein n is from about 3,000 to 3,400;

b. polyvinyl pyrrolidones of the formula:

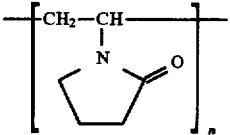

wherein n is from about 100 to 360;

c. acrylamide/acrylate/butylaminoethyl methacrylate polymers;

d. vinyl acetate/crotonic acid/vinyl neodacanoate terpolymers;

e. vinyl acetate/crotonic acid copolymers; and f. terpolyamides comprised of the copolymerization products of dicarboxylic acid-diamine reaction product, a second but dissimilar dicarboxylic acid-diamine reaction product and a lactim wherein said terpolyamides have a molecular weight of from about 12,000 to about 24,000.

The method of making the braided dental floss may comprise the steps of applying the wax from a bath of molten wax to the braided threads.

The method may further include the steps of introducing an additive to the wax bath and stirring the wax bath in order to achieve a uniform concentration of the additive therein.

As illustrated by the foregoing description, the present invention has superior application as a dental floss for cleaning teeth. The braided dental floss of the present invention has increased tensile strength, improved cleaning efficiencies, greater resistance to fraying and superior comfort.

The terms and expressions which have been employed are used as terms of description and not of limitation, and there is no intention in the use of such terms or expressions of excluding any equivalence of the features shown and described as portions thereof, it being recognized that various modifications are possible without departing from the spirit or the intent of the invention.

We claim:

1. A dental cleaning floss comprising an odd number of multiple threads, said threads each comprised of a plurality of strands twisted together, wherein said odd number of threads are braided together and include a first number of threads selected from a first group consisting of nylon, polyester, polyethylene, PTFE, PFA, and mixtures thereof and a second number of threads selected from a complement of the first group.

* * * * *